United States Patent [19]
Fong et al.

[11] Patent Number: 5,484,886
[45] Date of Patent: Jan. 16, 1996

[54] HUMAN NEUROKININ-1 RECEPTOR

[75] Inventors: Tung M. Fong, Somerset; Catherine D. Strader, Verona, both of N.J.

[73] Assignee: Merck & Co., Inc., Rahway, N.J.

[21] Appl. No.: 117,965

[22] Filed: Sep. 7, 1993

Related U.S. Application Data

[63] Continuation of Ser. No. 691,197, Apr. 25, 1991, abandoned.
[51] Int. Cl.$^6$ .................... C12N 15/12; C07K 14/435; C07K 14/71
[52] U.S. Cl. ........................................ 530/350; 435/69.1
[58] Field of Search ............................ 530/350; 514/12, 514/21; 435/69.1, 240.2, 320.1; 536/23.5

[56] References Cited

FOREIGN PATENT DOCUMENTS

WO92/16547  10/1992  WIPO.

OTHER PUBLICATIONS

O'Hara, et al., *PNAS*, 86: 5673–5677, 1989.
Takeda, et al., *Biochem & Biophys. Res. Commun.*, 179(3), 1232–40 (1991).
*Patent Abstracts of Japan*, 015(341), 29 Aug. 91 (JP3133998).
C. A. Maggi, et al., *J. Auton. Pharmacol.*, 13, 23–93 (1993), "Review: Tachykinin receptors and tachykinin receptor antagonists".
D. Regoli, et al. *Life Sci.*, 54(26), 2035–2047 (1994), "Minireview: Neurokinin Receptor Subtypes Characterized By Biological Assays".
B. S. Sachais, et al., *J. Biol. Chem.*, 268(4), 2319–2323 (1993), "Molecular Basis for the Species Selectivity of the Substance P Antagonist CP–96,345".
C. D. Strader, et al., *Annual Rev. Biochem.*, 63, 101–132 (1994), "Structure and Function of G Protein–Coupled Receptors".
G–X. Xie et al., *Proc. Nat. Acad. Sci.*, 89:4124–4128 (1992), "Expression cloning of a cDNA encoding a seven–helix receptor from human placenta with a high affinity for opioid ligands".
Buell, et al., "Molecular Characterisation, Expression and Localisation of Human Neurokinin–3 Receptor", *Febs. Lett.*, 299, No. 1, 90–95 (1992).
Cascieri, et al., "Characterization of the Substance P Receptor in Rat Brain Cortex Membranes . . . ", *J. Biol. Chem.*, 258, 5158–5164 (1983).
Fong, et al. (I), "Differential Activation of Intracellular Effector by Two Isoforms of Human Neurokinin–1 Receptor", *Mol. Pharm.*, 41, 24–30 (1992).
Fong, et al. (II), "Molecular Basis for the Species Selectivity of the Neurokinin–1 Receptor Antagonists . . . ", *J. Biol.*, 267(36), 25668–671 (1992).
Gerard, et al. (I), "The Human Neurokinin A (Substance K) Receptor", *J. Biol. Chem.*, 265, 20455–62 (1990).
Gerard, et al., (II), "Molecular Cloning and Chromosomal Lacalization of the Human Substance P Receptor Gene", *FASEB J.*, 5(5), 4647 (1991).

Gerard, et al. (III), "Human Substance P Receptor (NK–1): Organization of the Gene, Chromosome . . . ", *Biochem.* 30(44), 10640–46 (1991).
Guan, et al., "Identification of a Single Amino Acid Residue Responsible for the Binding of a Class of Beta–Adrenergic . . . ", *Mol. Pharm.*, 41, 695–698 (1992).
Hershey, et al., "Molecular Characterization of a Functional cDNA Encoding the Rat Substance P Receptor", *Science*, 247, 958–962 (1990).
Hopkins, et al., "Isolation and Characterization of the Human Lung NK–1 Receptor cDNA", *Biochem, Biophys. Res. Commun.*, 180, 1110–1117 (1991).
Kobilka, et al., "cDNA for the Human 2–Adrenergic Receptor: A Protein with Multiple Membrane . . . ", *Proc., Natl. Acad. Sci.*, USA, 84, 46–50 (1987).
Laneuville, et al., "Characterization of the Effects Produced by Neurokinins and Three Agonists Selective for Neurokinin . . . ", *Life Sci.*, 42, 1295–1305 (1988).
lundblad, et al., "Origin and Distribution of Capsaicin, Sensitive Substance P–Immunoreactive . . . ", *Acta Otolaryngol*, 96, 485–493 (1983).
Masu, et al., "cDNA Cloning of Bovine Substance–K Receptor Through Oocyte Expression System", *Nature*, 329, 836–838 (1987).
McLean, et al., "Activity and Distribution of Binding Sites in Brain of a Nonpeptide Substance P (NK1) Receptor Antagonist", *Science*, 251, 437–439 (1991).
Oksenberg, et al., "A Single Amino–Acid Difference Confers Major Pharmacological Variation Between Human and Rodent 5–HT1B Receptors", *Nature*, 360, 161–163 (1992).
Payan, et al., "Specific Stimulation of Human T Lymphocytes by Substance P", *J. Immunol.*, 131, 1613–15 (1983).
Sachais, et al., "Molecular Basis for the Species Selectivity of the Substance P Antagonist CP–96,345", *J. Biol. Chem.*, 268 (4), 2319–23 (1993).
Sasai, et al., "Molecular Characterization of Rat Substance K Receptor and Its mRNAs", *Biochem. Biophys. Res. Commun.*, 165, 695–702 (1989).
Shigemoto, et al., "Cloning and Expression of Rat Neuromedin K Receptor cDNA", *J. Biol. Chem.*, 265, 623–628 (1990).

(List continued on next page.)

Primary Examiner—Marianne P. Allen
Attorney, Agent, or Firm—J. Eric Thies; David L. Rose

[57] ABSTRACT

Recombinant human neurokinin-1 receptor (hereinafter identified as human NK1R) has been prepared by polymerase chain reaction techniques. The complete sequence of human NK1R complementary DNA has been identified. Expression systems, including a CHO (chinese hamster ovarian cell line) stable expression system; and an assay using the CHO expression system have been developed. NK1R, also known as substance P receptor, may be used in an assay to identify and evaluate entities that bind to the substance P receptor. The assay may also be used in conjunction with diagnosis and therapy to determine the body fluid concentration of substance P antagonists in arthritis patients.

1 Claim, 9 Drawing Sheets

OTHER PUBLICATIONS

Shigetada, "Substance P Receptor and Gene Thereof", *Patent Abstracts of Japan,* 015(341), 29 Aug. 91, (JP3133998).

Suryanarayana, et al., "A Point Mutation in the Seventh Hydrophobic Domain of the a2 Adrenergic Receptor . . . ", *J. Biol. Chem.,* 266 (23), 15488–15492 (1991).

Takeda, et al., "Molecular Cloning, Structural Characterization & Functional Expression of the Human Substance P Receptor", *Biochem. & Biophys. Res. Comm.,* 179(3), 1232–40 (1991).

Yokata, et al., "Molecular Charaterization of a Functional cDNA for Rat Substance P Receptor", *J. Biol. Chem.,* 264, (30) 17649–52 (1989).

Hershey, et al., "Molecular and Genetic Characterization, Functional Expression, and mRNA Expression . . . ", *Ann. of the N.Y. Acad. of Sciences,* vol. 632, pp. 63–78 (1991).

Ohkubo, et al., "Molecular Characterization of the Three Tachykinin Receptors", *Ann. of the N.Y. Acad. of Sciences,* vol. 632. pp. 53–62 (1991).

Regali, et al., "Receptors for Substance P and Related Neurokinins", *Pharmacology,* vol. 38(1), pp. 1–15 (1989).

Tschida, "Tissue Distribution and Quantitation of the mRNAs for Three Rat Tachykinin Receptors", *Eur. Jour. Biochem.,* vol. 193, pp. 751–757 (1990).

Hershey, et al., "Organization, Structure, and Expression of the Gene Encoding the Rat Substance P Receptor", *J. Biol. Chem.,* vol. 266, pp. 4366–4374 (1991).

McGillis, et al., "Immunoaffinity Purification of Membrane Protein Constituents of the IM–9 Lymphoblast Receptor for Substance P", *Anal. Biochem.,* 164,502–513 (1987).

Pascual, et al., "Antipeptide Antibodies That Recognize a Lymphocyte Substance P Receptor", *J. Immunol.,* 143(11) 3697–3702 (1989).

Gerard et al., Biochemistry, vol. 30, pp. 10640–10646, 1991.

Pascual et al., J. of Immunology, vol. 143, No. 11, pp. 3697–3702, Dec. 1, 1989.

Hopkins et al., Biochem. Biophys. Res. Commn., vol. 180 No. 2, Oct. 31, 1991.

McGillis et al., Analytical Biochem., vol. 164, pp. 502–513, 1987.

Fong et al., Molecular Pharmacology, vol. 41, pp. 24–30, 1991.

Yo Kata et al., J. Biol Chem, 264, pp. 17649–17652, 1989.

U.S. Ser. No. 691,198 filed Apr. 25, 1991 to Fong et al.

U.S. Ser. No. 691,200 filed Apr. 25, 1991 to Fong et al.

Met Asp Asn Val Leu Pro Val Asp Ser Asp Leu Ser Pro Asn Ile Ser Thr Asn Thr Ser
                                        10                                      20
Glu Pro Asn Gln Phe Val Gln Pro Ala Trp Gln Ile Val Leu Trp Ala Ala Ala Tyr Thr
                                        30                                      40
Val Ile Val Val Thr Ser Val Val Gly Asn Val Val Val Met Trp Ile Ile Leu Ala His
                                        50                                      60
Lys Arg Met Arg Thr Val Thr Asn Tyr Phe Leu Val Asn Leu Ala Phe Ala Glu Ala Ser
                                        70                                      80
Met Ala Ala Phe Asn Thr Val Val Asn Phe Thr Tyr Ala Val His Asn Glu Trp Tyr Tyr
                                        90                                     100
Gly Leu Phe Tyr Cys Lys Phe His Asn Phe Phe Pro Ile Ala Ala Val Phe Ala Ser Ile
                                       110                                     120

FIG. 1a    SEQ ID NO:26

```
                    130                                     140
Tyr Ser Met Thr Ala Val Ala Phe Asp Arg Tyr Met Ala Ile Ile His Pro Leu Gln Pro
                    150                                     160
Arg Leu Ser Ala Thr Ala Thr Lys Val Val Ile Cys Val Ile Trp Val Leu Ala Leu Leu
                    170                                     180
Leu Ala Phe Pro Gln Gly Tyr Tyr Ser Thr Thr Glu Thr Met Pro Ser Arg Val Val Cys
                    190                                     200
Met Ile Glu Trp Pro Glu His Pro Asn Lys Ile Tyr Glu Lys Val Tyr His Ile Cys Val
                    210                                     220
Thr Val Leu Ile Tyr Phe Leu Pro Leu Leu Val Ile Gly Tyr Ala Tyr Thr Val Val Gly
                    230                                     240
Ile Thr Leu Trp Ala Ser Glu Ile Pro Gly Asp Ser Ser Asp Arg Tyr His Glu Gln Val
```

FIG. 1b

```
                                                                            260
Ser Ala Lys Arg Lys Val Val Val Lys Met Met Ile Val Val Val Cys Thr Phe Ala Ile Cys
             250                                                                            280

Trp Leu Pro Phe His Ile Phe Phe Leu Pro Tyr Ile Asn Pro Asp Leu Tyr Leu Lys
                         270                                                    300

Lys Phe Ile Gln Gln Val Tyr Leu Ala Ile Met Trp Leu Ala Met Ser Ser Thr Met Tyr
                                 290                                                320

Asn Pro Ile Ile Tyr Cys Cys Leu Asn Asp Arg Phe Arg Leu Gly Phe Lys His Ala Phe
                     310                                                    340

Arg Cys Cys Pro Phe Ile Ser Ala Gly Asp Tyr Glu Gly Leu Glu Met Lys Ser Thr Arg
                             330                                                360

Tyr Leu Gln Thr Gln Gly Ser Val Tyr Lys Val Ser Arg Leu Glu Thr Thr Ile Ser Thr
                                     350

FIG. 1c
```

```
                                              370                         380                         390                         400
Val Val Gly Ala His Glu Glu Pro Glu Asp Gly Pro Lys Ala Thr Pro Ser Ser Leu Asp Leu Thr Ser Asn Cys Ser Ser Arg Ser Asp Ser Lys Thr Met Thr Glu Ser Phe Ser
       407
Phe Ser Ser Asn Val Leu Ser
```

FIG. 1d

```
         10         20         30         40         50         60         70
GAAAAGCCT  TCCACCCTCC TGTCTGGCTT TAGAAGGACC CTGAGCCCCA GGCGCCACGA CAGGACTCTG 80         90        100        110        120        130        140
CTGCCAGAGG GGGTTGTGTA CAGATAGTAG GGCTTTACCG CCTAGCTTCG AAATGGATAA CGTCCTCCCG 150        160        170        180        190        200        210
GTGGACTCAG ACCTCTCCCC AAACATCTCC ACTAACACCT CGGAACCCAA TCAGTTCGTG CAACCAGCCT 220        230        240        250        260        270        280
GGCAAATTGT CCTTTGGGCA GCTGCCTACA CGGTCATTGT GGTGACCTCT GTGGTGGGCA ACGTGGTAGT 290        300        310        320        330        340        350
GATGTGGATC ATCTTAGCCC ACAAAAGAAT GAGGACAGTG ACGAACTATT TTCTGGTGAA CCTGGCCTTC 360        370        380        390        400        410        420
GCGGAGGCCT CCATGGCTGC ATTCAATACA GTGGTGAACT TCACCTATGC TGTCCACAAC GAATGGTACT
```

FIG. 2a    SEQ ID NO:27

```
          430        440        450        460        470        480        490
ACGGCCTGTT CTACTGCAAG TTCCACAACT TCTTCCCCAT CGCCGGCTGTC TTCGCCAGTA TCTACTCCAT 500        510        520        530        540        550        560
GACGGCTGTC GCCTTTGATA GGTACATGGC CATCATACAT CCCCTCCAGC CCCGGCTGTC AGCCACAGCC 570        580        590        600        610        620        630
ACCAAAGTGG TCATCTGTGT CATCTGGGTC CTGGCTCTCC TGCTGGCCTT CCCCCAGGGC TACTACTCAA 640        650        660        670        680        690        700
CCACAGAGAC CATGCCCAGC AGAGTCCTGT GCATGATCGA ATGGCCAGAG CATCCGAACA AGATTTATGA 710        720        730        740        750        760        770
GAAAGTGTAC CACATCTGTC TGACTGTGCT GATCTACTTC CTCCCCCTGC TGGTGATTGG CTATGCATAC 780        790        800        810        820        830        840
ACCGTAGTGG GAATCACACT ATGGGCCAGT GAGATCCCCG GGACTCCTC TGACCGCTAC CACGAGCAAG
```

FIG. 2b

```
     850        860        870        880        890        900        910
TCTCTGCCAA GCGCAAGGTG GTCAAAATGA TGATTGTCGT GGTGTGCACC TTCGCCATCT GCTGGCTGCC 920        930        940        950        960        970        980
CTTCCACATC TTCTTCCTCC TGCCCTACAT CAACCCAGAT CTCTACCTGA AGAAGTTTAT CCAGCAGGTC 990       1000       1010       1020       1030       1040       1050
TACCTGGCCA TCATGTGGCT GGCCATGAGC ACAACCCCAT CATCTACTGC TGCCTTCAATG 1060       1070       1080       1090       1100       1110       1120
ACAGGTTCCG TCTGGGCTTC AAGCATGCCT TCCGGTGCTG CCCCTTCATC AGCGCCGGGG ACTATGAGGG 1130       1140       1150       1160       1170       1180       1190
GCTGGAAATG AAATCCACCC GGTATCTCCA GACCCAGGGC AGTGTGTACA AAGTCAGCCG CCTGGAGACC 1200       1210       1220       1230       1240       1250       1260
ACCATCTCCA CAGTGGTGGC GGCCCACGAG GAGGAGCCAG AGGACGGCCC CAAGGCCACA CCCTCGTCCC
```

FIG. 2c

```
       1270       1280       1290       1300       1310       1320       1330
TGGACCTGAC CTCCAACTGC TCTTCACGAA GTGACTCCAA GACCATGACA GAGAGCTTCA GCTTCTCCTC 1340       1350       1360       1370       1380       1390       1400
CAATGTGCTC TCCTAGGCCA CAGGGCCTTT GGCAGGTGCA GCCCCCACTG CCTTTGACCT GCCTCCCTTC 1410       1420       1430       1440       1450       1460       1470
ATGCATGGAA ATTCCCTTCA TCTGGAACCA TCAGAAACAC CCTCACACTG GGACTTGCAA AAAGGGTCAG 1480       1490       1500       1510       1520       1530       1540
TATGGGTTAG GGAAAACATT CCATCCTTGA GTCAAAAAAT CTCAATTCTT CCCTATCTTT GCCACCCTCA 1550       1560       1570       1580       1590       1600       1610
TGCTGTGTGA CTCAAACCAA ATCACTGAAC TTTGCTGAGC CTGTAAAATA AAAGGTCGGA CCAGCTTTC 1620       1630       1640       1650       1660       1670       1679
CCAAAAGCCC ATTCATTCCA TTCTGGAAGT GACTTTGGCT GCATGCCAGT GCTCATTTCA GGATGAATT
```

FIG. 2d

HUMAN NEUROKININ-1 RECEPTOR

This is a continuation of application Ser. No. 07/691,197, filed on Apr. 25, 1991, now abandoned.

BACKGROUND OF THE INVENTION

The present invention concerns cloned human neurokinin-1 receptor (human NK1R) and recombinant human NK1R. Neurokinin-1 receptor is also known as substance P receptor.

J. Yokota, et al., J. Biol. Chem., 264:17649 (1989) have reported cloned rat neurokinin-1 receptor. N. P. Gerard, et al., J. Biol. Chem., 265:20455 (1990), have reported human neurokinin-2 receptor. Cloned rat and bovine neurokinin-2 receptor have likewise been reported. See respectively, Y. Sasi, and S. Nakanishi, Biochem Biophys. Res. Comm., 165:695 (1989), and Y. Masu, et al., Nature 329:836 (1987). Cloned rat neurokinin-3 receptor has also been reported by R. Shigemoto, et al., J. Biol. Chem., 265:623 (1990).

The above references, however, neither disclose or suggest the instant invention. In particular, the pharmacological profile of the human receptor differs significantly from the rat. Moreover, the rat neurokinin-1 receptor differs from the NK1R disclosed herein by 23 amino acids.

Substance P is a naturally occuring undecapeptide belonging to the tachykinin family of peptides. Substance P is a pharmacologically-active neuropeptide that is produced in mammals. Its characteristic amino acid sequence is illustrated in U.S. Pat. No. 4,680,283. As is well known in the art substance P and other tachykinins have been implicated in the pathophysiology of numerous diseases. Substance P has been shown to be involved in the transmission of pain or migraine (see B. E. B. Sandberg et al., *Journal of Medicinal Chemistry*, Vol. 25, p. 1009 (1982)), as well as in central nervous system disorders such as anxiety and schizophrenia, in respiratory and inflammatory diseases such as asthma and rheumatoid arthritis, respectively, and in gastrointestinal disorders and diseases of the GI tract, like ulcerative colitis and Crohn's disease, etc. (see D. Regoli in "Trends in Cluster Headache," edited by F. Sicuteri et al., Elsevier Scientific Publishers, Amsterdam, 1987, pp. 85–95).

The instant invention also concerns an assay protocol which can be used to determine substance P activity in body fluids. The assay can also be used for identifying and evaluating substances that bind substance P receptor. Thus, the assay can be used to identify substance P antagonists and evaluate their binding affinity. Other methods includes that described by M. A. Cascieri, et al., J. Biol. Chem., 258–5158 (1983).

By use of such methods, substance P antagonists have been identified. See, for example, R. M. Snider, et al., Science, 251:435 (January 1991) and S. McLean, et al., Science, 251:437 (January 1991). See also WO90/05525 which published May 31, 1990, which is hereby incorporated by reference. Methods to date have proven inferior, in part, for failure of the animal receptor (animal NK1R, NK2R or NK3R) activity to accurately reflect that of human neurokinin-1 receptor. Furthermore, prior to this disclosure human NK1R has not been available in a purified form or in substantial isolation from NK2R and/or NK3R.

Use of such neurokinin receptor sources can not accurately depict the affinity for human NK1R.

BRIEF DESCRIPTION OF THE DRAWINGS

FIG. 1 Full length amino acid sequence of human neurokinin-1 receptor.

FIG. 2 Full length nucleotide sequence of the cloned human neurokinin-1 receptor complementary DNA.

SUMMARY OF THE INVENTION

Figure 3:
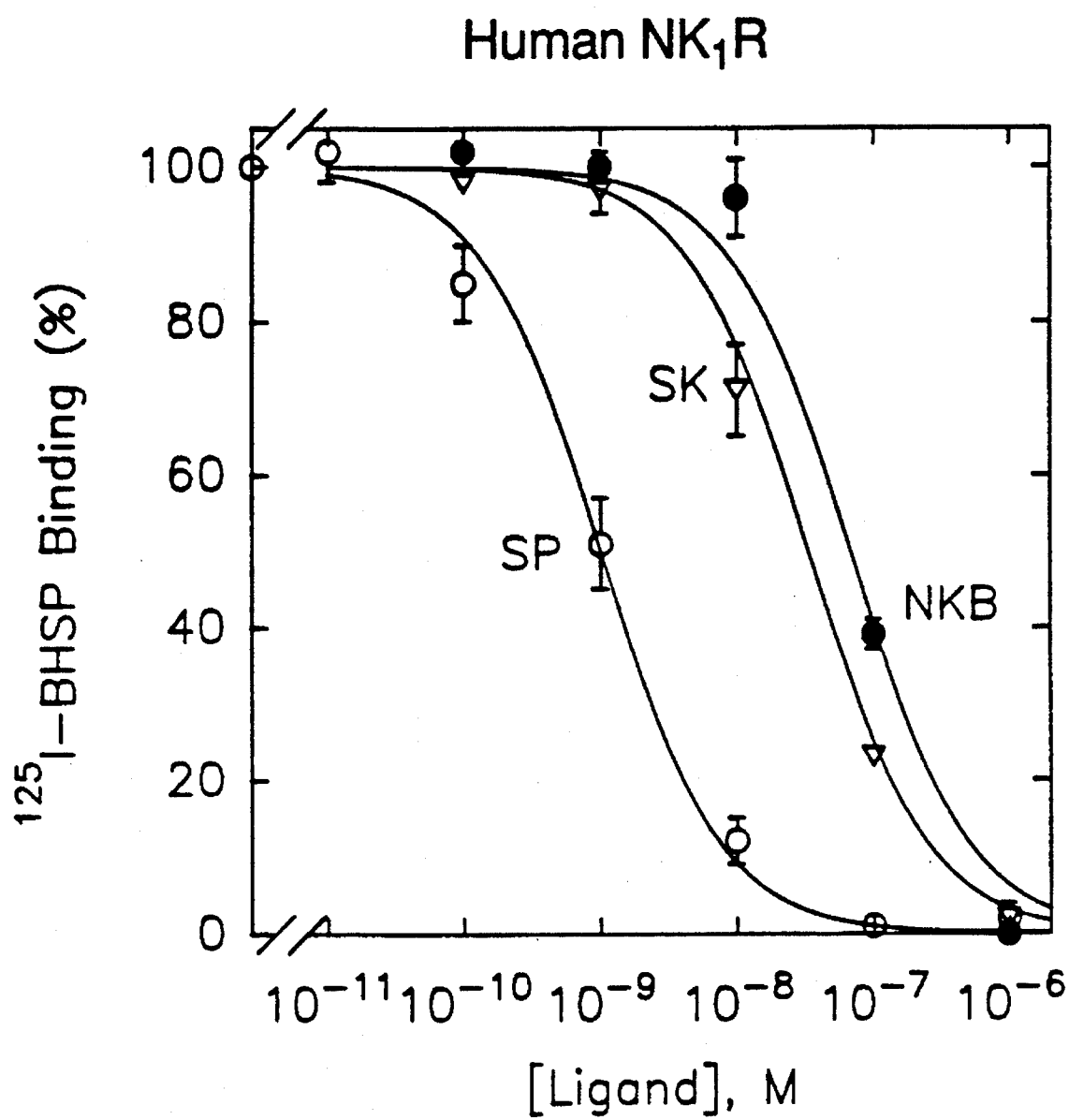
FIG. 3 Competitive binding of substance P (SP), substance K (SK) and human neurokinin-1 receptor (NK1R) in COS assay.

Recombinant human neurokinin-1 receptor (human NK1R) is disclosed which has been prepared by polymerase chain reaction techniques. Also disclosed is the complete sequence of human NK1R complementary DNA; expression systems, including a CHO (chinese hamster ovarian cell line) stable expression system; and an assay using the CHO expression system.

NK1R, also known as substance P receptor, can be used in an assay to identify and evaluate entities that bind substance P receptor. The assay can also be used in conjunction with diagnosis and therapy to determine the body fluid concentration of substance P in arthritis patients.

DETAILED DESCRIPTION OF THE INVENTION

One embodiment of the invention concerns human neurokinin-1 receptor, said receptor being free of other human receptor proteins.

In one class this embodiment concerns human neurokinin-1 receptor, said receptor being free of other human proteins.

Within this class, this embodiment concerns human neurokinin-1 receptor from human cells such as glioblastoma, said receptor being free of other proteins.

In a second class, this embodiment concerns a protein comprising the 407 amino acid sequence depicted in FIG. 1, said protein being free of other human receptor proteins.

Within the second class this embodiment concerns a protein consisting of the 407 amino acid sequence as shown in FIG. 1.

The first embodiment also concerns a pharmaceutical composition for inhibiting the binding of substance P to cellular neueokinin-1 receptor, said composition comprising an effective amount of neurokinin-1 receptor.

The first embodiment also concerns a method of inhibiting the binding of substance P to cellular human neurokinin-1 receptor, in a patient in need of such inhibition, comprising: administration of an effective amount of human neurokinin-1 receptor.

The use of such pharmaceutical compositions and methods for antagonising the binding of substance P to in vivo neurokinin-1 receptor is disclosed in, for example, R. M. Snider, et al., Science, 251:435 (January 1991); S. McLean, et al., Science, 251:437 (January 1991); and WO90/05525 which published May 31, 1990, which are hereby incorporated by reference.:

A second embodiment concerns a DNA sequence encoding human neurokinin receptor complementary DNA, said DNA, said sequence being free of other human DNA sequences.

As will be appreciated by those of skill in the art, there is a substantial amount of redundancy in the set of condons which translate specific amino acids. Accordingly, the invention also includes alternative base sequences wherein a codon (or codons) are replaced with another codon, such that the amino acid sequence translated by the DNA sequence remains unchanged. For purposes of this specification, a sequence bearing one or more such replaced codons will be defined as a degenetate variation. Also included are mutations (exchange of individual amino acids) which one of skill in the art would expect to have no effect on functionality, such as valine for leucine, arginine for lysine and asparigine for glutamine.

One class of the second embodiment the invention concerns the nucleotide sequence of complementary DNA, beginning with nucleotide 123 and ending with necleotide 1346 as shown in FIG. 2.

Within this class of the second embodiment is the DNA sequence (SEQ ID NO:1) that further comprises:

```
           10          20          30
    GAAAAAGCCT TCCACCCTCC TGTCTGGCTT 40          50          60
    TAGAAGGACC CTGAGCCCCA GGCGCCACGA 70          80          90
    CAGGACTCTG CTGCAGAGGG GGGTTGTGTA 100         110         120
    CAGATAGTAG GGCTTTACCG CCTAGCTTCG

122
    AA
``` or a degenerate variation thereof.

The second embodiment the invention concerns the partial nucleotide sequence of complementary DNA, as shown in FIG. 2 or a degenerate variation thereof.

A third embodiment of this invention concerns systems for expressing human neurokinin receptor.

One class this third embodiment of the invention comprises:

A plasmid which comprises:
(a) a mammalian expression vector, such as pRcCMV, and
(b) a base sequence encoding human neurokinin-1 receptor protein.

Within this class of the third embodiment the neurokinin-1 receptor comprises the nucleotide sequence of complementary DNA, beginning with nucleotide 123 and ending with necleotide 1346 as shown in FIG. 2.

A second class of this third embodiment of the invention concerns a system for the transient expression of human neurokinin-1 receptor (NK1R) in a monkey kidney cell line (COS).

A third class of this third embodiment of the invention concerns a system for the expression of human neurokinin-1 receptor in a chinese hamster ovarian cell line (CHO), the system comprising a vector comprising human neurokinin receptor (NK1R) cDNA.

Within this class of the third embodiment is is the sub-class wherein the expression system includes A plasmid which comprises:
(a) a mammalian expression vector, such as pRcCMV, and
(b) a base sequence encoding human neurokinin-1 receptor protein.

Within this sub-class the neurokinin-1 receptor comprises the nucleotide sequence of complementary DNA, beginning with nucleotide 123 and ending with necleotide 1346 as shown in FIG. 2. is subclosed into the vector pRcCMV.

A forth embodiment of the invention concerns a method of using any of the above expression systems for determining the binding affinity of a test sample for human neurokinin-1 receptor.

In one class this embodiment concerns a method of using a Chinese hamster ovarian cell line, said line transplanted with a plasmid, which plasmid comprises:
(a) vector pRcCMV, and
(b) the base sequence encoding human neurokinin-1 receptor protein, the method which comprises:
  (1) expressing human neurokinin-1 receptor in said CHO cells;
  (2) addition of a test sample to a solution containing $^{125}$I-substance p and said cells;
  (3) incubating the products of Step (1), wherein said incubation effective for expressing said the human neurokinin-1 receptor and effective for competitive binding of said $^{125}$I-substance P and said test sample to said human neurokinin-1 receptor;
  (4) separating said $^{125}$I-substance P which is bound to said human neurokinin-1 receptor from said $^{125}$I-substance P which is not bound;
  (5) measuring the radioactivity of said $^{125}$I-substance P which is bound to said human neurokinin-1 receptor.

In a second class this embodiment concerns a method of using a Chinese hamster ovarian cell line (CHO), said line transplanted with a plasmid which plasmid comprises
(a) vector pRcCMV, and
(b) the base sequence encoding human neurokinin-1 receptor protein, the method comprising:
  (1) expressing human neurokinin-1 receptor in said CHO cells;
  (2) equilibrating the product of Step (1) with $^3$H-myo-inositol;
  (3) washing the product of Step (2);
  (4) incubating the product of Step (3) with a test sample in the presence of 10 mM LiCl, which results in the production of inositol monophosphate;
  (5) measuring the inositol monophosphate.

In overview, the present invention describes methods to isolate the human neurokinin-1 receptor (human NK1R) complementary DNA (cDNA) without prior knowledge of its protein sequence or gene sequence. Human NK1R is a membrane receptor for the neurotransmitter substance P. Polymerase chain reaction (PCR) technique was utilized for the isolation of human NK1R cDNA. In the approach, the regions of rat NK1R Applicants thought to be similar to human NK1R were identified, oligonucleotide primers corresponding to those region were designed, PCR amplification was carried out to obtain part of the NK1R cDNA from human cells, and its DNA sequence was determined. The remaining part of the human NK1R cDNA was obtained from a human cDNA library utilizing the above sequence information of human NK1R cDNA.

The complete sequence of the human NK1R cDNA was determined, and its encoded protein sequence was deduced. Among other things, such sequence information is useful in the process of developing novel substance P antagonists.

Three heterologous expression systems were used to express the cloned human NK1R cDNA. The Xenopus oocyte expression enables one to determine the biological function of human NK1R. The COS (a monkey kidney cell line) expression can be used to measure the ligand binding properties of human NK1R. The CHO (a Chinese hamster ovarian cell line) stable expression is suitable for natural product screen to identify potential therapeutic agent or other substances that bind to substance P receptor. This cell line can also be used as an assay kit for determining the body fluid concentration of substance P in arthritis patients.

Assay protocols use the heterologously expressed human NK1R for determination of the binding affinity and antagonistic activity of substance P antagonists.

1) Isolation of human NK1R cDNA

To isolate the human NK1R cDNA in the absence of its sequence information, we developed methods to obtain three separate but overlapping cDNA clones in three steps. (i) We have adopted the homologous cloning strategy (Ohara et al., 1989, Proc. Nat. Acad. Sci., 86:5673–5677) to isolate cDNA clones encoding the central core region of human NK1R with the assumption that the human NK1R sequence is similar to the published sequence (Yokota et al., 1989, J. Biol. Chem., 264:17649–17652) of rat NK1R in certain areas where appropriate PCR primers can be designed. Degenerate primers corresponding to the rat sequence were used in PCR amplification (Mullis and Faloona, 1987, Meth. Enzymol., 155:335) to obtain the cDNA encoding the central trnsmembrane core region of human NK1R from human mRNA. (ii) After determining the sequence of the core region in human NK1R, new primers corresponding to the human sequence were designed and a second homologous PCR amplification was performed using the human primer in the core region with degenerate primers corresponding to the N-terminal sequence of rat NK1R. The cDNA encoding the N-terminal region of human NK1R was thus obtained from human mRNA and its sequence was determined. (iii) An anchored PCR strategy was developed to isolate the cDNA encoding the C-terminal region of human NK1R, in which primers corresponding to the core region of human NK1R were used in combination with a primer corresponding to the sequence of a cloning vector to obtain the cDNA from a human cDNA library.

To confirm the authenticity of the cDNA encoding human NK1R, an independent PCR amplification was performed to obtain the full length cDNA in a single step using primers from the 5' and 3' untranslated regions.

2) Expression of the cloned human NK1R

Three expression systems were developed for the cloned human NK1R. An transient expression in Xenopus oocytes resulted from microinjection of in vitro transcribed mRNA from the cloned cDNA (Xenopus Laevis from XENOPUS ONE, Ann Arbor, Mich.). This system allows the measurement of biological effect of NK1R activation upon ligand binding. Another transient expression in COS (a monkey kidney cell line, ATCC CRL 1651, ATCC Rockville Md.) resulted from the transfection of the cloned cDNA under the control of vital promoter into mammalian cells (e.g., COS). The transfected cells are suitable for determination binding affinity of human NK1R for various ligands. Stable expression of human NK1R in mammalian cells (e.g., CHO, a Chinese hamster ovarian cell line, ATCC CRL 9096, ATCC Rockville Md.) was achieved after integration of the transfected cDNA into the chromosomes of the host cells. These stable cell lines will constitutively express the cloned human NK1R and can be propagated infinitely. Therefore, stable expression system is very useful in large scale drug screen, and can be used to determine substance p concentration in the biopsy sample of patients.

To establish a stable cell line expressing the cloned human NK1R, the cDNA was subcloned into the vector pRcCMV (INVITROGEN).

The electrophysiological assay of human NK1R expressed in Xenopus oocytes was based on the fact that NK1R activates the phospholipase C upon substance P binding, and phospholipase C in turn increases the intracellular calcium concentration through inositol trisphosphate ($IP_3$) and $IP_3$-gated calcium channel on intracellular membranes. The calcium increase activates calcium-gated chloride channels on plasma membranes which gives rise to a chloride current measurable by two electrode voltage clamp.

The binding assay of human NK1R expressed in COS or CHO is based on the use of $^{125}I$-substance P ($^{125}I$-SP, from DU PONT, Boston, Mass.) as a radioactively labeled ligand which compete with unlabeled substance p or any other ligand for binding to the human NK1R. Monolayer cell culture of COS or CHO was dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific $^{125}I$-SP binding (approximately 50,000 to 200,000 cells).

The activation of phospholipase C by NK1R can also be measured in CHO cells by determining the accumulation of inositol monophosphate which is a degradation product of $IP_3$.

In addition to large scale drug screening using the stable CHO cell line expressing the cloned human NK1R, other alternative applications are obvious. For example, the stable cell line can be used in the binding assay to determine the substance p concentration from biopsy samples. The human NK1R protein can also be injected into patients to reduce substance P concentration in some neurogenic inflammatory diseases.

EXAMPLE 1

Step A:

In the first step of obtaining the cDNA encoding the central core region of human NK1R, human mRNA was prepared from three human glioblastoma cell lines T98G, CCF-STTG1 and U87MG (obtained from the American Type Culture Collection, Rockville, Md.) by the FAST-TRACK method (INVITROGEN, San Diego, Calif.). Synthesis of first strand cDNA from 4 ug of human mRNA was initiated by oligo (dT) primers in a total volume of 20 ul according to protocols of the BRL cDNA synthesis system (BRL, LIFE TECHNOLOGIES, Inc., Gaithersburg, Md.). Ten ul of the first strand cDNA was used as template with three rat primers (50 pmol rspr2s4, 50 pmol rspr2s4h, and 100 pmol rspr7a2; see Table I for their sequences) in a primary PCR amplification in a total volume of 100 ul according to the GENEAMP protocol (PERKIN ELMER CETUS, Norwalk, Conn.). Thirty cycles of PCR were performed using the following parameters: 1 min of denaturation at 94° C., 2 min of annealing at 40° C. and 4 min of extension at 72° C. with 2 sec of auto extension. Ten ul of the primary PCR product was used as template with the same primers in a secondary PCR amplification under the same cycling conditions to further amplify the DNA. Ten ul of the secondary PCR product was used as template with three rat primers (50 pmol rspr2s4, 50 pmol rspr2s4h, 50 pmol rspr7al and 50 pmol rspr7alh) in 30 cycles of tertiary PCR amplification with the following parameters: 1 min of denaturation at 94° C., 2 min of-annealing at 45° C., and 4 min of extension at 72° C. with 2 sec of auto extension. The tertiary PCR product was analyzed by agarose gel electrophoresis and was found to contain a 600 bp DNA fragment. This DNA fragment was excised from the gel, purified by GENECLEAN (Bio 101, La Jolla, Calif.), phosphorylated, and subcloned into Sma I site of the plasmid vector BLUE-SCRIPT SK+ (STRATAGENE, La Jolla, Calif.). The DNA sequence was determined by the Sequenase dideoxy chain termination method (USBC, Cleveland, Ohio). Sequence alignment analysis showed that this cDNA fragment is similar (90% identity at nucleotide level) to the central core region of rat NK1R from amino acid 91 to 280.

STEP B:

After determination of the core region sequence of human NK1R, five antisense primers were synthesized based on the human sequence (hspr3a5, hspr5a1, hspr5a2, hspr6a1 and hspr6a2; see Table II for their sequences). These primers would be used to obtain the N-terminal cDNA sequence of human NK1R. One ug of human glioblastoma mRNA and 6 uM of each of the above primers was used in first strand cDNA synthesis in a total volume of 20 ul according the BRL cDNA synthesis protocols. The cDNA was extracted by phenol-chloroform, precipitated by ethanol and dissolved in 30 ul of water. Ten ul of the cDNA was used as template with two rat primers (50 pmol rsprn and 50 pmol rsprnh) and one human primer (150 pmol hspr3a5) in the primary PCR amplification in a total volume of 100 ul. Thirty cycles were performed with the following parameters: 1 min denaturation at 94° C., 1 min of annealing at 55° C., and 3 min of extension at 72° C. Five ul of the primary PCR product was then used as template with two rat primers (50 pmol rsprn and 50 pmol rsprnh) and one human primer (100 pmol hspr3a4) in 30 cycles of secondary PCR amplification with the same parameters. Two ul of the secondary PCR product was used as template with two rat primers (50 pmol rsprn and 50 pmol rsprnh) and one human primer in 30 cycles of tertiary PCR amplification with the same parameters. The tertiary PCR product was analyzed by agarose gel electrophoresis and was found to contain a 500 bp fragment. This DNA fragment can hybridize with a human oligonucleotide (hspr3a2), indicating it is not a non-specific by-product. This DNA fragment was excised from the gel, purified by GENECLEAN (Bio 101), phosphorylated, and subcloned into Sma I site of the vector Bluescript SK+. DNA sequence analysis revealed that this fragment encodes the human NK1R N-terminal region and it also contains 5' untranslated sequence.

STEP C:

In the third step, an anchored PCR protocol was developed in which the cDNA encoding the C-terminal region of human NK1R was obtained from a cDNA library using sense human primers and a primer corresponding to the vector sequence. Three ug of human glioblastoma mRNA was primed by 2.5 ug of oligo (dT) in the first strand cDNA synthesis in a total volume of 50 ul, followed by second strand cDNA synthesis according the BRL cDNA synthesis protocols. The cDNA product was then heated at 70° C. for 10 min. The yield of double stranded cDNA was determined by incorporating 1.25 uM of $^{32}$P-a-dCTP as tracer in the reaction. Four ul of T4 DNA polymerase was added to the reaction mixture and incubated at 37° C. for 10 min. The reaction was stopped by adding 16 ul of 250 mM EDTA, extracting with phenol/CHCl$_3$, and precipitating with ethanol. The cDNA was dissolved in 50 ul of HE buffer (10 mM HEPES-1mM EDTA). Small size cDNA was removed by the Select-D(RF) SPIN COLUMN (5'TO3', Boulder, Colo.), and the large size cDNA was precipitated by ethanol and dissolved in 36 ul of water. Four ul of 0.2M Tris-10 mM spermidine-1 mM EDTA (pH7.5) was added to the tube and heated at 70° C. for 1 min. The cDNA was phosphorylated by adding 5 ul of blunt-end kinase buffer (0.5M Tris pH 9.5, 0.1M MgCl$_2$, 50 mM DTT, 50% glycerol), 2.5 ul of 10 mMATP, 2.5 ul of polynucleotide kinase, and incubating at 37° C. for 30 min. The cDNA was extracted by phenol/ CHCl$_3$, precipitated by ethanol and ligated to EcoRI linker according to the PROMEGA ECORI linker ligation protocol (PROMEGA, Madison, Wis.). Linker-ligated cDNA was then ligated to calf intestinal phosphatase-treated EcoRI site of the vector BLUESCRIPT SK+. One ul of the ligated plasmid DNA was used as template in 30 cycles of primary PCR with two human primers (50 pmol hspr6s1 and 50 pmol hspr6s2) and 100 pmol of vector-specific primer t3 (obtained from STRATAGEE) with the following parameters: 1 min of denaturation at 94° C., 2 min of annealing at 55° C., and 4 min of extension at 72° C. with 2 sec auto extension. One ul of the primary PCR product was used in 30 cycles of secondary PCR amplification with one human primer (100 pmol hspr6s3) and the same vector-specific primer t3 under the same conditions. One ul of the secondary PCR product was used in 30 cycles of tertiary PCR amplification with one human primer (100 pmol hspr6s4) and 100 pmol of vector-specific primer SK (STRATAGEE) under the same conditions. A 780 bp DNA fragment was detected which also hybridized to a human oligo probe hspr6s5. This DNA fragment was excised from the agarose gel, purified by GENECLEAN (BIO 101), phosphorylated, and subcloned into Sma I site of the vector BLUESCRIPT SK+. DNA sequence analysis revealed that it encodes the C-terminal region of human NK1R and contains 3' untranslated sequence.

STEP D:

Since three separate but overlapping cDNA clones encoding human NK1R were isolated above and the possibility of alternative pre-mRNA splicing exists, it is necessary to confirm the authenticity of the full length cDNA sequence by isolating a full length cDNA directly. Based on the above sequence in the untranslated region, primers were synthesized which should give rise to a full length cDNA. Using the PERKIN ELMER CETUS RNA PCR amplification kit (Perkin Elmer Cetus), cDNA was synthesized from 1.5 ug of human glioblastoma mRNA in a total volume of 20 ul with 50 pmol of the human primer hspr3uta5. One half of the first strand cDNA was used as template in 30 cycles of primary PCR amplification with two human primers (50 pmol hspr3uta5, 50 pmol hspr5uts1) with the following parameters: 1 min of denaturation at 94° C., 2 min of annealing at 55° C., and 4 min of extension at 55° C. with 2 sec auto extension. Ten ul of the primary PCR product was used as template in 30 cycles of secondary PCR amplification with two human primers (50 pmol hspr3uta6 and 50 pmol hspr5uts2) under the same conditions. A 1350 bp DNA fragment was excised from agarose gel, purified by GENECLEAN (BIO 101), digested with restriction endonucleases with EcoRI and Not I, and subcloned into the vector BLUESCRIPT SK+. DNA sequence analysis confirmed the general structure of the cloned human NK1R cDNA. The sequence of human NK1R CDNA is shown in FIG. 2.

| Name | Sequence (SEQ ID NO:_:) | Position | Direction |
|---|---|---|---|
| rspr2s4 | TGCATGGCTGCATTCAAT (2) | 238–255 | sense |

-continued

| Name | Sequence (SEQ ID NO:_:) | Position | Direction |
|---|---|---|---|
| rspr2s4h | TGCATGGCTGCCTTCAA (3) | 238–254 | sense |
| rspr7a2 | ACAGTAGATGATGGGGTTGTACAT (4) | 918–894 | antisense |
| rspr7a1 | CAGGTAGACCTGCTGGATGAACTT (5) | 864–841 | antisense |
| rspr7a1h | CAGGTACACCTGCTGGATGAACTT (6) | 864–841 | antisense |
| rsprn | ATGGATAACGTCCTTCCTAT (7) | 1–20 | sense |
| rsprnh | ATGGACAATGTGCTGCCCA (8) | 1–19 | sense |

| Name | Sequence (SEQ ID NO:_:) | Position | Direction |
|---|---|---|---|
| hspr3a2 | GAAGAAGTTGTGGAACTTGCA (9) | 455–435 | antisense |
| hspr3a1 | CATGGAGTAGATACTGGCGAA (10) | 491–471 | antisense |
| hspr3a4 | GGATGTATGATGGCCATGTA (11) | 532–513 | antisense |
| hspr3a5 | ACTTTGGTGGCTGTGGCTGA (12) | 568–549 | antisense |
| hspr5a1 | ATGCATAGCCAATCACCAGCA (13) | 768–748 | antisense |
| hspr5a2 | CATAGTGTGATTCCCACTAC (14) | 793–774 | antisense |
| hspr6a1 | TGCACACCACGACAATCATCA (15) | 888–868 | antisense |
| hspr6a2 | TTGATGTAGGGCAGGAGGAA (16) | 943–924 | antisense |
| hspr6s1 | GCAAGTCTCTGCCAAGCGCAA (17) | 836–856 | sense |
| hspr6s2 | TGATGATTGTCGTGGTGTGCA (18) | 868–888 | sense |
| hspr6s3 | TTCCACATCTTCTTCCTCCT (19) | 912–931 | sense |
| hspr6s4 | CTACATCAACCCAGATCTCT (20) | 935–954 | sense |
| hspr6s5 | TCTCTACCTGAAGAAGTT (21) | 950–967 | sense |
| hspr12uta1 | CAAGGATGGAATGTTTTCCCT (22) | 1499–1479 | antisense |
| hspr12uta2 | (GACATGCGGCCGC)AACCCATACTGACCCTTTT(23) | 1478–1460 | antisense |
| hspr5uts1 | CCTCCTGTCTGGCTTTAGAA (24) | 16–35 | sense |
| hspr5uts2 | (GCGCAGAATTC)GTGTACAGATAGTAGGCTT (25) | 86–105 | sense |

Expression in Xenopus oocytes

To express the human NK1R cDNA in Xenopus oocytes, the cDNA was cloned into an in vitro transcription vector BLUESCRIPT SK+ (STRATAGENE) which contains the T7 promoter for initiation of T7 RNA polymerase catalyzed RNA synthesis. One ug of linear plasmid DNA which contained the human NK1R cDNA downstream of the T7 promoter was used in the in vitro transcription reaction containing 40 mM Tris pH 7.5, 50 mM NaCl, 8 mM MgCl$_2$, 2 mM spermidine, 0.4 mM CTP, 0.4 mM ATP, 0.4 mM UTP, 0.16 mM GTP, 2.5 ul CAP analog (STRATAGENE), 30 mM DTT, 1 U RNase Block II (STRATAGENE), 0.83 pmol $^{32}$P-a-CTP and 25 U of T7 RNA polymerase. The reaction tube was incubated at 37° C. for 1 hour. Usually 5 ug of RNA was synthesized as quantitated by incorporation of $^{32}$P-a-CTP into RNA. After RNA synthesis, the plasmid DNA was removed by adding 10 U of RNase free DNase and 1 U of RNase Block II. The reaction mixture was extracted by phenol/CHCl$_3$, and the unincorporated nucleotides were removed by the Select-D(RF) spin column (5'T03'). The RNA transcript was precipitated by ethanol twice and dissolved in RNase free water. Oocytes were removed from Xenopus frogs, treated with 2 mg/ml collagenase (specific activity<0.3 U/mg, BOEHRINGER MANNHEIM, Indianapolis, Ill.) in OR-2 buffer (82.5 mM NaCl, 2 mM KCl, 1 mMMECl$_2$, 5 mMHEPES, pH 7.4) for 4 hours at 19° C. The dissociated oocytes were incubated in OR-2 buffer supplemented by 1.8 mM CaCl$_2$, 0.5 mg/ml gentamycin and 0.5 mM theophylline at 19° C. overnight before injection. A 50 nl aliquot contain 2 ng of RNA transcript was injected into each oocyte. The injected oocytes Were incubated at 19° C. for 2 days before electrophysiological recording (see Example 3 for assay method).

Expression in COS

To express the human NK1R transiently in COS, the cDNA was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 millions COS cells was achieved by electropotation in 800 ul of transfection buffer (135 mM NaCl, 1.2 mM CaCl$_2$, 1.2 mM MgCl$_2$, 2.4 mM K$_2$HPO$_4$, 0.6 mM KH$_2$PO$_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100U/ml penicillin-streptomycin, and 90% DMEM media (GIBCO, Grand Island, N.Y.) in 5% CO$_2$ at 37° C. for three days before the binding assay.

Stable Expression in CHO

To establish a stable cell line expressing the cloned human NK1R, the cDNA was subcloned into the vector pRcCMV (INVITROGEN). Transfection of 20 ug of the plasmid DNA into CHO cells was achieved by electropotation in 800 ul of transfection buffer suplemented with 0.625 mg/ml Herring sperm DNA at 300 V and 950 uF using the IBI GENEZA-PPER (IBI). The transfected cells were incubated in CHO media [10% fetal calf serum, 100 U/ml penniciline-streptomycin, 2 mM glutamine, 1/500 hypoxanthine-thymidine (ATCC), 90% IMDM media (3RH BIOSCIENCES, Lenexa, Kans.), 0.7 mg/ml G418 (GIBCO)] in 5% CO$_2$ at 37° C. until colonies were visible. Each colony was separated and propagated. The cell clone with the highest number of human NK1R was selected for subsequent application in the assay of Example 3.

EXAMPLE 3

Assay Protocol Using Oocytes

The oocyte was voltage-clamped at −80 mV by the model 8500 intracellular preamp-clamp (DAGAN, Minneapolis, Minn.). The recoding chamber was continuously perfused with recording buffer (96 mM $NaCl_1$, 2 mM KCl, 1.8 mM $CaCl_2$, 5 mM HEPES, pH 7.4). Chloride current was elicited by applying substance P (from 0.1 nM to 1000 nM) to the recording chamber. At least three oocytes were measured for each concentration. The antagonistic activity of any potential substance P antagonist can be assessed by determining the inhibition of substance P response. Likewise, NK1 agonists can be identified by their ability to stimulate a response in oocytes injected with NK1R mRNA but not in uninjected oocytes.

Assay Protocol using COS or CHO

The binding assay of human NK1R expressed in COS or CHO is based on the use of $^{125}$I-substance P ($^{125}$I-SP, from DU PONT, Boston, Mass.) as a radioactively labeled ligand which compete with unlabeled substance p or any other ligand for binding to the human NK1R. Monolayer cell culture of COS or CHO was dissociated by the non-enzymatic solution (SPECIALTY MEDIA, Lavallette, N.J.) and resuspended in appropriate volume of the binding buffer (50 mM Tris pH 7.5, 5 mM$MnCl_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific $^{125}$I-SP binding (approximately 50,000 to 200,000 cells). In the binding assay, 200 ul of cells were added to a tube containing 20 ul of 1.5 to 2.5 nM of $^{125}$I-SP and 20 11 of unlabeled substance p or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter. Illustrative of this method of using these expression systems are the results shoen in FIG. 3. These results show the competitive binding of substance P (SP), substance K (SK) and human neurokinin-1 receptor (NK1R) in the COS assay.

ALTERNATIVE PROTOCOL

The activation of phospholipase C by NK1R can also be measured in CHO cells by determining the accumulation of inositol monophosphate which is a degradation product of $IP_3$. CHO cells were seeded in 12-well plate at 250,000 cells per well. After incubating in CHO media for 4 days, cells were loaded with 0.025 uCi/ml of $^3$H-myoinositol by overnight incubation. The extracellular radioactivity was removed by washing with phosphate buffered saline. LiCl was added to the well at final concentration of 0.1 mM with or without antagonist, and continued incubation at 37° C. for 15 min. Substance p was added to the well at final concentration of 0.3 nM to activate the human NK1R. After 30 min of incubation at 37° C., the media was removed and 0.1N HCl was added. Each well was sonicated at 4° C. and extracted with $CHCl_3$/methanol (1:1). The aqueous phase was applied to a 1 ml Dowex AG 1X8 ion exchange column. The column was washed with 0.1N formic acid followed by 0.025M ammonium formate-0.1N formic acid. The inositol monophosphate was eluted with 0.2M ammonium formate-0.1N formic acid and quantitated by beta counter.

---

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 122 base pairs
        ( B ) TYPE: nucleic acid
        ( C ) STRANDEDNESS: single
        ( D ) TOPOLOGY: linear ( i i ) MOLECULE TYPE: cDNA to mRNA ( i x ) SEQUENCE DESCRIPTION: SEQ ID NO:1:

```
GAAAAAGCCT  TCCACCCTCC  TGTCTGGCTT  TAGAAGGACC  CTGAGCCCCA           5 0

GGCGCCACGA  CAGGACTCTG  CTGCAGAGGG  GGGTTGTGTA  CAGATAGTAG         1 0 0

GGCTTTACCG  CCTAGCTTCG  AA                                          1 2 2
```

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:2:

```
TGCATGGCTG  CATTCAAT                                                  1 8
```

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:3:

TGCATGGCTG CCTTCAA                       17

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:4:

ACAGTAGATG ATGGGGTTGT ACAT               24

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:5:

CAGGTAGACC TGCTGGATGA ACTT               24

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:6:

CAGGTACACC TGCTGGATGA ACTT               24

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:7:

ATGGATAACG TCCTTCCTAT                    20

( 2 ) INFORMATION FOR SEQ ID NO:8:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE:

( x i ) SEQUENCE DESCRIPTION: SEQ ID NO:8:

ATGGACAATG TGCTGCCCA　　　　　　　　　　　　　　　　　　　　　　　　　19

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:9:

GAAGAAGTTG TGGAACTTGC A　　　　　　　　　　　　　　　　　　　　　　21

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:10:

CATGGAGTAG ATACTGGCGA A　　　　　　　　　　　　　　　　　　　　　　21

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:11:

GGATGTATGA TGGCCATGTA　　　　　　　　　　　　　　　　　　　　　　　20

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:12:

ACTTTGGTGG CTGTGGCTGA　　　　　　　　　　　　　　　　　　　　　　　20

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single (D) TOPOLOGY: linear (ii) MOLECULE TYPE:

(xi) SEQUENCE DESCRIPTION: SEQ ID NO:13:

ATGCATAGCC AATCACCAGC A 21

(2) INFORMATION FOR SEQ ID NO:14:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE:

(xi) SEQUENCE DESCRIPTION: SEQ ID NO:14:

CATAGTGTGA TTCCCACTAC 20

(2) INFORMATION FOR SEQ ID NO:15:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE:

(xi) SEQUENCE DESCRIPTION: SEQ ID NO:15:

TGCACACCAC GACAATCATC A 21

(2) INFORMATION FOR SEQ ID NO:16:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE:

(xi) SEQUENCE DESCRIPTION: SEQ ID NO:16:

TTGATGTAGG GCAGGAGGAA 20

(2) INFORMATION FOR SEQ ID NO:17:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE:

(xi) SEQUENCE DESCRIPTION: SEQ ID NO:17:

GCAAGTCTCT GCCAAGCGCA A 21

(2) INFORMATION FOR SEQ ID NO:18:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE:

( x i ) SEQUENCE DESCRIPTION: SEQ ID NO:18:

TGATGATTGT CGTGGTGTGC A    21

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:19:

TTCCACATCT TCTTCCTCCT    20

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:20:

CTACATCAAC CCAGATCTCT    20

( 2 ) INFORMATION FOR SEQ ID NO:21:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:21:

TCTCTACCTG AAGAAGTT    18

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:22:

CAAGGATGGA ATGTTTTCCC T    21

( 2 ) INFORMATION FOR SEQ ID NO:23:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:23:

AACCCATACT GACCCTTTT    19

(2) INFORMATION FOR SEQ ID NO:24:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE:

(xi) SEQUENCE DESCRIPTION: SEQ ID NO:24:

CCTCCTGTCT GGCTTTAGAA      20

(2) INFORMATION FOR SEQ ID NO:25:

(i) SEQUENCE CHARACTERISTICS:
  (A) LENGTH: 19 base pairs
  (B) TYPE: nucleic acid
  (C) STRANDEDNESS: single
  (D) TOPOLOGY: linear (ii) MOLECULE TYPE:

(xi) SEQUENCE DESCRIPTION: SEQ ID NO:25:

GTGTACAGAT AGTAGGCTT      19

(2) INFORMATION FOR SEQ ID NO:26:

(i) SEQUENCE CHARACTERISTICS:
  (A) LENGTH: 407 amino acids
  (B) TYPE: amino acid
  (C) STRANDEDNESS: single
  (D) TOPOLOGY: linear (ii) MOLECULE TYPE:

(xi) SEQUENCE DESCRIPTION: SEQ ID NO:26:

```
Met Asp Asn Val Leu Pro Val Asp Ser Asp Leu Ser Pro Asn Ile Ser
 1               5                  10                  15

Thr Asn Thr Ser Glu Pro Asn Gln Phe Val Gln Pro Ala Trp Gln Ile
            20                  25                  30

Val Leu Trp Ala Ala Ala Tyr Thr Val Ile Val Val Thr Ser Val Val
            35                  40                  45

Gly Asn Val Val Val Met Trp Ile Ile Leu Ala His Lys Arg Met Arg
    50                  55                  60

Thr Val Thr Asn Tyr Phe Leu Val Asn Leu Ala Phe Ala Glu Ala Ser
65                  70                  75                  80

Met Ala Ala Phe Asn Thr Val Val Asn Phe Thr Tyr Ala Val His Asn
                85                  90                  95

Glu Trp Tyr Tyr Gly Leu Phe Tyr Cys Lys Phe His Asn Phe Phe Pro
            100                 105                 110

Ile Ala Ala Val Phe Ala Ser Ile Tyr Ser Met Thr Ala Val Ala Phe
            115                 120                 125

Asp Arg Tyr Met Ala Ile Ile His Pro Leu Gln Pro Arg Leu Ser Ala
            130                 135                 140

Thr Ala Thr Lys Val Val Ile Cys Val Ile Trp Val Leu Ala Leu Leu
145                 150                 155                 160

Leu Ala Phe Pro Gln Gly Tyr Tyr Ser Thr Thr Glu Thr Met Pro Ser
                165                 170                 175

Arg Val Val Cys Met Ile Glu Trp Pro Glu His Pro Asn Lys Ile Tyr
                180                 185                 190
```

|   |   |   |   |   |   |   |   |   |   |   |   |   |   |
|---|---|---|---|---|---|---|---|---|---|---|---|---|---|
| Glu | Lys | Val<br>195 | Tyr | His | Ile | Cys | Val<br>200 | Thr | Val | Leu | Ile<br>205 | Tyr | Phe | Leu | Pro |
| Leu | Leu<br>210 | Val | Ile | Gly | Tyr<br>215 | Ala | Tyr | Thr | Val | Val<br>220 | Gly | Ile | Thr | Leu | Trp |
| Ala<br>225 | Ser | Glu | Ile | Pro | Gly<br>230 | Asp | Ser | Ser | Asp | Arg<br>235 | Tyr | His | Glu | Gln | Val<br>240 |
| Ser | Ala | Lys | Arg | Lys<br>245 | Val | Val | Lys | Met | Met<br>250 | Ile | Val | Val | Val<br>255 | Cys | Thr |
| Phe | Ala | Ile | Cys<br>260 | Trp | Leu | Pro | Phe | His<br>265 | Ile | Phe | Phe | Leu<br>270 | Leu | Pro | Tyr |
| Ile | Asn | Pro<br>275 | Asp | Leu | Tyr | Leu | Lys<br>280 | Lys | Phe | Ile | Gln<br>285 | Gln | Val | Tyr | Leu |
| Ala | Ile<br>290 | Met | Trp | Leu | Ala | Met<br>295 | Ser | Ser | Thr | Met<br>300 | Tyr | Asn | Pro | Ile | Ile |
| Tyr<br>305 | Cys | Cys | Leu | Asn | Asp<br>310 | Arg | Phe | Arg | Leu | Gly<br>315 | Phe | Lys | His | Ala | Phe<br>320 |
| Arg | Cys | Cys | Pro | Phe<br>325 | Ile | Ser | Ala | Gly | Asp<br>330 | Tyr | Glu | Gly | Leu | Glu<br>335 | Met |
| Lys | Ser | Thr | Arg<br>340 | Tyr | Leu | Gln | Thr | Gln<br>345 | Gly | Ser | Val | Tyr | Lys<br>350 | Val | Ser |
| Arg | Leu | Glu<br>355 | Thr | Thr | Ile | Ser | Thr | Val<br>360 | Val | Gly | Ala | His | Glu<br>365 | Glu | Glu |
| Pro | Glu<br>370 | Asp | Gly | Pro | Lys | Ala<br>375 | Thr | Pro | Ser | Ser | Leu<br>380 | Asp | Leu | Thr | Ser |
| Asn<br>385 | Cys | Ser | Ser | Arg | Ser<br>390 | Asp | Ser | Lys | Thr | Met<br>395 | Thr | Glu | Ser | Phe | Ser<br>400 |
| Phe | Ser | Ser | Asn | Val<br>405 | Leu | Ser | | | | | | | | | |

( 2 ) INFORMATION FOR SEQ ID NO:27:

( i ) SEQUENCE CHARACTERISTICS:
        ( A ) LENGTH: 1679 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:27:

```
GAAAAAGCCT TCCACCCTCC TGTCTGGCTT TAGAAGGACC CTGAGCCCCA GGCGCCACGA      60
CAGGACTCTG CTGCAGAGGG GGGTTGTGTA CAGATAGTAG GGCTTTACCG CCTAGCTTCG     120
AAATGGATAA CGTCCTCCCG GTGGACTCAG ACCTCTCCCC AAACATCTCC ACTAACACCT     180
CGGAACCCAA TCAGTTCGTG CAACCAGCCT GGCAAATTGT CCTTTGGGCA GCTGCCTACA     240
CGGTCATTGT GGTGACCTCT GTGGTGGGCA ACGTGGTAGT GATGTGGATC ATCTTAGCCC     300
ACAAAGAAT GAGGACAGTG ACGAACTATT TTCTGGTGAA CCTGGCCTTC GCGGAGGCCT     360
CCATGGCTGC ATTCAATACA GTGGTGAACT TCACCTATGC TGTCCACAAC GAATGGTACT     420
ACGGCCTGTT CTACTGCAAG TTCCACAACT TCTTCCCCAT CGCCGCTGTC TTCGCCAGTA     480
TCTACTCCAT GACGGCTGTG GCCTTTGATA GGTACATGGC CATCATACAT CCCCTCCAGC     540
CCCGGCTGTC AGCCACAGCC ACCAAAGTGG TCATCTGTGT CATCTGGGTC CTGGCTCTCC     600
TGCTGGCCTT CCCCCAGGGC TACTACTCAA CCACAGAGAC CATGCCCAGC AGAGTCGTGT     660
GCATGATCGA ATGGCCAGAG CATCCGAACA AGATTTATGA GAAAGTGTAC CACATCTGTG     720
```

| | | | | | | |
|---|---|---|---|---|---|---|
| TGACTGTGCT | GATCTACTTC | CTCCCCCTGC | TGGTGATTGG | CTATGCATAC | ACCGTAGTGG | 780 |
| GAATCACACT | ATGGGCCAGT | GAGATCCCCG | GGGACTCCTC | TGACCGCTAC | CACGAGCAAG | 840 |
| TCTCTGCCAA | GCGCAAGGTG | GTCAAAATGA | TGATTGTCGT | GGTGTGCACC | TTCGCCATCT | 900 |
| GCTGGCTGCC | CTTCCACATC | TTCTTCCTCC | TGCCCTACAT | CAACCCAGAT | CTCTACCTGA | 960 |
| AGAAGTTTAT | CCAGCAGGTC | TACCTGGCCA | TCATGTGGCT | GGCCATGAGC | TCCACCATGT | 1020 |
| ACAACCCCAT | CATCTACTGC | TGCCTCAATG | ACAGGTTCCG | TCTGGGCTTC | AAGCATGCCT | 1080 |
| TCCGGTGCTG | CCCCTTCATC | AGCGCCGGCG | ACTATGAGGG | GCTGGAAATG | AAATCCACCC | 1140 |
| GGTATCTCCA | GACCCAGGGC | AGTGTGTACA | AAGTCAGCCG | CCTGGAGACC | ACCATCTCCA | 1200 |
| CAGTGGTGGG | GGCCCACGAG | GAGGAGCCAG | AGGACGGCCC | CAAGGCCACA | CCCTCGTCCC | 1260 |
| TGGACCTGAC | CTCCAACTGC | TCTTCACGAA | GTGACTCCAA | GACCATGACA | GAGAGCTTCA | 1320 |
| GCTTCTCCTC | CAATGTGCTC | TCCTAGGCCA | CAGGGCCTTT | GGCAGGTGCA | GCCCCCACTG | 1380 |
| CCTTTGACCT | GCCTCCCTTC | ATGCATGGAA | ATTCCCTTCA | TCTGGAACCA | TCAGAAACAC | 1440 |
| CCTCACACTG | GGACTTGCAA | AAAGGGTCAG | TATGGGTTAG | GGAAAACATT | CCATCCTTGA | 1500 |
| GTCAAAAAAT | CTCAATTCTT | CCCTATCTTT | GCCACCCTCA | TGCTGTGTGA | CTCAAACCAA | 1560 |
| ATCACTGAAC | TTTGCTGAGC | CTGTAAAATA | AAAGGTCGGA | CCAGCTTTTC | CCAAAAGCCC | 1620 |
| ATTCATTCCA | TTCTGGAAGT | GACTTGGCT | GCATGCGAGT | GCTCATTTCA | GGATGAATT | 1679 |

What is claimed is:

1. A recombinant protein having the amino acid sequence SEQ ID NO:26 of the human neurokinin-1 receptor.

* * * * *